US00PP18451P2

(12) United States Plant Patent
Miyazaki

(10) Patent No.: US PP18,451 P2
(45) Date of Patent: Jan. 22, 2008

(54) ***PHLOX* PLANT NAMED 'SUNPHLOBURU'**

(50) Latin Name: *Phlox drummondii*
Varietal Denomination: Sunphloburu

(75) Inventor: Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/518,580

(22) Filed: Sep. 8, 2006

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Phlox* plant named 'Sunphloburu', characterized by its compact and mounding plant habit; vigorous growth habit; freely branching habit; light purple-colored flowers with dark purple-colored central star; freely and continuous flowering habit; and good garden performance.

1 Drawing Sheet

Botanical designation: *Phlox drummondii.*
Cultivar denomination: 'Sunphloburu'.

BACKGROUND OF THE INVENTION

The present invention relates to a new and distinct cultivar of *Phlox,* botanically known as *Phlox drummondii* and hereinafter referred to by the name 'Sunphloburu'.

The new *Phlox* is a product of a planned breeding program conducted by the Inventor in Shiga, Japan. The objective of the breeding program was to create new compact *Phlox* cultivars with attractive flower coloration.

The new *Phlox* originated from a cross-pollination made by the Inventor in June, 2002, in Shiga, Japan, of a proprietary selection of *Phlox drummondii* identified as code number 2Ph-45a, not patented, as the female, or seed, parent with a proprietary selection of *Phlox drummondii* identified as code number 2Ph-45b, not patented, as the male, or pollen, parent. The new *Phlox* was discovered and selected by the Inventor as a single flowering plant within the progeny of the stated cross-pollination in a controlled environment in Shiga, Japan.

Asexual reproduction of the new *Phlox* by vegetative cuttings in a controlled environment in Shiga, Japan since October, 2004, has shown that the unique features of this new *Phlox* are stable and reproduced true to type in successive generations.

SUMMARY OF THE INVENTION

The cultivar Sunphloburu has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunphloburu'. These characteristics in combination distinguish 'Sunphloburu' as a new and distinct cultivar of *Phlox:*

1. Compact and mounding plant habit.
2. Vigorous growth habit.

3. Freely branching habit.
4. Light purple-colored flowers with dark purple-colored central star.
5. Freely and continuous flowering habit.
6. Good garden performance.

Compared to plants of the parent selections, plants of the new *Phlox* are more compact and differ in flower coloration.

Plants of the new *Phlox* can also be compared to plants of the cultivar Parona Light Blue, not patented. In side-by-side comparisons conducted in Shiga, Japan, plants of the new *Phlox* and the cultivar Parona Light Blue differed in the following characteristics:

1. Plants of the new *Phlox* were more spreading and broader than plants of the cultivar Parona Light Blue.
2. Plants of the new *Phlox* were more vigorous than plants of the cultivar Parona Light Blue.
3. Plants of the new *Phlox* were more freely branching than plants of the cultivar Parona Light Blue.
4. Plants of the new *Phlox* had smaller leaves than plants of the cultivar Parona Light Blue.
5. Plants of the new *Phlox* were more freely flowering than plants of the cultivar Parona Light Blue.
6. Plants of the new *Phlox* and the cultivar Parona Light Blue differed in flower color.

BRIEF DESCRIPTION OF THE PHOTOGRAPHS

The accompanying colored photographs illustrate the overall appearance of the new *Phylox,* showing the colors as true as it is reasonably possible to obtain in colored reproductions of this type. Colors in the photographs may differ slightly from the color values cited in the detailed botanical description which accurately describe the colors of the new *Phlox.*

The photograph at the top of the sheet comprises a side perspective view of a typical flowering plant of 'Sunphloburu' grown in a container.

The photograph at the bottom of the sheet is a close-up view of typical flowers of 'Sunphloburu'.

DETAILED BOTANICAL DESCRIPTION

The aforementioned photograph and following observations, measurements and values describe plants grown in Shiga, Japan, under commercial practice during the spring in an outdoor nursery with day temperatures averaging 23° C. and night temperatures averaging 12° C. After planting, plants had been growing for about four months when the photographs and description were taken. In the following description, color references are made to The Royal Horticultural Society Colour Chart, 2001 Edition, except where general terms of ordinary dictionary significance are used.

Botanical classification: *Phlox drummondii* cultivar Sunphloburu.

Parentage:

*Female, or seed, parent.*—Proprietary selection of *Phlox drummondii* identified as code number 2Ph-45a, not patented.

*Male, or pollen, parent.*—Proprietary selection of *Phylox drummondii* identified as code number 2Ph-45b, not patented.

Propagation:

*Type.*—By vegetative cuttings.

*Time to initiate roots.*—About two to three weeks at 20° C. to 25° C.

*Time to produce a rooted young plant roots.*—About four to eight weeks at 20° C. to 25° C.

*Root description.*—Fine, fibrous; ivory white to pale brown in color.

*Rooting habit.*—Freely branching.

Plant description:

*Plant form/habit.*—Compact and mounded plant habit; outwardly spreading; vigorous growth habit. Freely branching habit; pinching enhances branching potential.

*Plant height.*—About 13.2 cm.

*Plant width* (*spread*).—About 55.2 cm.

*Lateral branches.*—Length: About 21.8 cm. Diameter: About 2 mm. Internode length: About 1.9 cm. Strength: Strong. Texture: Pubescent. Color: 146D.

Foliage description:

*Arrangement.*—Alternate, simple; sessile.

*Length.*—About 2.3 cm.

*Width.*—About 1.1 cm.

*Shape.*—Lanceolate.

*Apex.*—Acute.

*Base.*—Cordate.

*Margin.*—Entire.

*Texture, upper and lower surfaces.*—Pubescent.

*Venation pattern.*—Pinnate; reticulate.

*Color.*—Developing leaves, upper surface: 137C. Developing leaves, lower surface: N144D. Fully expanded leaves, upper surface: 137C; venation, 137C. Fully expanded leaves, lower surface: 147B; venation, 147B.

Flower description:

*Flower type/habit.*—Single rotate hypocraterimorphous flowers arranged in terminal and axillary cymes; flowers face obliquely upward. Panicles conical in shape. Freely flowering habit with about 290 flower buds and flowers developing per plant.

*Fragrance.*—Moderate.

*Natural flowering season.*—Continuously flowering from spring to late autumn in Shiga, Japan. Flowers not persistent.

*Postproduction longevity.*—Flowers last about five days on the plant.

*Flower buds.*—Height: About 1.8 cm. Diameter: About 3 mm. Shape: Clavate. Color: N82A.

*Inflorescence height.*—About 2.4 cm.

*Inflorescence diameter.*—About 5.4 cm.

*Flower diameter.*—About 3.1 cm.

*Flower depth.*—About 2.3 cm.

*Petals.*—Quantity per flower: Typically five in a single whorl; petals fused at the base into a narrow tube. Length: About 1.3 cm. Lobe width: About 1.5 cm. Shape: Broadly rhombic. Apex: Obtuse. Margin: Entire. Texture, upper and lower surfaces: Smooth, glabrous. Color: Developing petals, upper surface: 76B; star, N81A; eye, 83A. Developing petals, lower surface: 76B. Fully expanded petals, upper surface: 76B; star, N81A; eye, 83A. Fully expanded petals, lower surface: 76B.

*Sepals.*—Quantity per flower: Typically five in a single whorl, fused at base; star-shaped calyx. Length: About 4 mm. Width: About 1 mm. Shape: Lanceolate. Apex: Acute. Margin: Entire. Texture, upper and lower surfaces: Smooth, glabrous. Color, upper and lower surfaces: 137C.

*Peduncles.*—Length: About 2.4 cm. Diameter: About 1.1 mm. Texture: Pubescent. Color: 146D.

*Pedicels.*—Length: About 6 mm. Diameter: About 0.5 mm. Texture: Smooth, glabrous. Color: 146D.

*Reproductive organs.*—Stamens: Quantity per flower: Typically five. Stamen length: About 2 mm to 10 mm. Anther shape: Linear. Anther length: About 2 mm. Anther color: 9B. Pollen amount: Moderate. Pollen color: 13A. Pistils: Quantity per flower: One. Pistil length: About 3 mm. Stigma shape: Three-parted. Stigma color: 145D. Style length: About 1 mm. Style color: 145D. Ovary color: 143A.

*Seed/fruit.*—Seed and fruit development have not been observed.

Disease/pest resistance: Plants of the new *Phlox* have not been noted to be resistant to pathogens and pests common to *Phlox*.

Garden performance: Plants of the new *Phlox* have been observed to have good garden performance and tolerate rain, wind and temperatures from about 0° C. to about 35° C.

It is claimed:

1. A new and distinct *Phlox* plant named 'Sunphloburu' as illustrated and described.

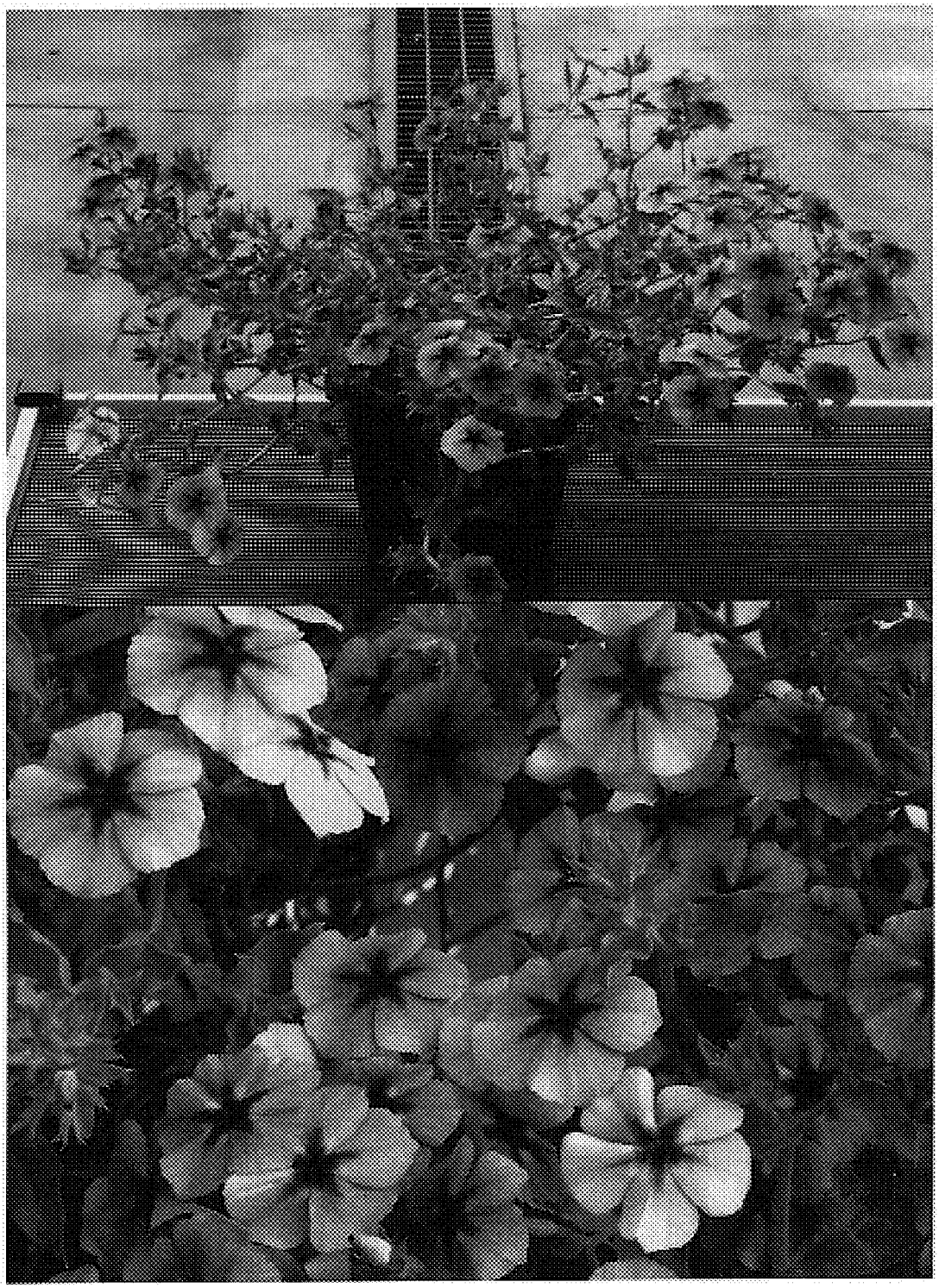

* * * * *